United States Patent [19]

Velker et al.

[11] 3,935,174

[45] Jan. 27, 1976

[54] 2-METHYLENE PROPANE PHOSPHONIC ACID ESTERS AND THEIR COPOLYMER WITH ACRYLONITRILE

[75] Inventors: Eugen Velker, Dormagen-Hackenbroich; Francis Bentz, Cologne; Gunther Nischk, Dormagen, all of Germany

[73] Assignee: Bayer Aktiengesellschaft, Leverkusen, Germany

[22] Filed: Aug. 20, 1974

[21] Appl. No.: 499,068

Related U.S. Application Data

[62] Division of Ser. No. 311,413, Dec. 1, 1972.

[30] Foreign Application Priority Data

Dec. 3, 1971    Germany............................ 2160019

[52] U.S. Cl............................ 260/80.71; 260/85.5 R
[51] Int. Cl.$^2$............. C08F 210/00; C08F 220/42; C08F 220/70, C08F 220/02
[58] Field of Search ......... 260/80.71, 80 PS, 85.5 R

[56] References Cited
UNITED STATES PATENTS

| | | | |
|---|---|---|---|
| 2,636,027 | 7/1953 | Coover et al.................... | 260/80 PS |
| 3,062,792 | 11/1962 | McConnell et al.............. | 260/80 PS |
| 3,312,674 | 4/1967 | Welch ............................. | 260/80 PS |

*Primary Examiner*—Joseph I. Schofer
*Assistant Examiner*—Herbert J. Lilling
*Attorney, Agent, or Firm*—Plumley & Tyner

[57] ABSTRACT

2-methylene propane phosphonic acid esters and their copolymers with acrylonitrile are the objects of the invention. The fibers produced from the copolymers are flame-resistant and show increased thermal stability, improved affinity for dyes and fastness to light. The copolymers of acrylonitrile and 2-methylene propane phosphonic acid esters - in addition to other comonomers - are produced by polymerizing the monomers in solution or - preferably - in an aqueous suspension or emulsion. Formed articles, such as fibres from said copolymers can be prepared by spinning a solution of the copolymer in an organic solvent p.i. in dimethyl formamide.

9 Claims, No Drawings

2-METHYLENE PROPANE PHOSPHONIC ACID ESTERS AND THEIR COPOLYMER WITH ACRYLONITRILE

This is a division of application, Ser. No. 311,413, filed Dec. 1, 1972.

This invention relates to 2-methylene propane phosphonic acid esters and to acrylnitrile copolymers which contain 2-methylene propane phosphonic acid in copolymerized form in addition to other comonomers such as (meth) acrylic acid esters, 2-methylene propane-1,3-dichloride, vinyl chloride, vinylidene chloride or mixtures of these comonomers.

The invention also relates to a process for producing the aforementioned copolymers and to films, fibers, filaments and moldings obtained therefrom.

The object of the invention are 2-methylene propane phosphonic acid esters of the formula

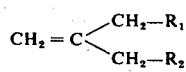

wherein $R_1$ represents halogen (Cl, Br, I) or the radical

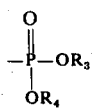

and $R_2$ the radical

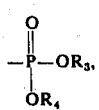

where
$R_3$ is hydrogen, $NH_4$ an alkalimetal, a $C_1$-$C_4$-alkyl, an aryl, halogen aryl or alkylaryl radical and $R_4$ hydrogen, a $C_1$-$C_4$-alkyl, an aryl, halogenaryl, or an alkylaryl radical.

1-Halogen-2-methylenepropane-3-phosphonic acid diesters or 2-methylenepropane-1,3-bis-phosphonic acid tetra-esters are prepared by reacting 1,3-dihalogen-2-methylene propane with triesters of phosphorous acid at elevated temperature the reaction may be effected in an organic solvent. For example, the reaction takes place in accordance with the following scheme:

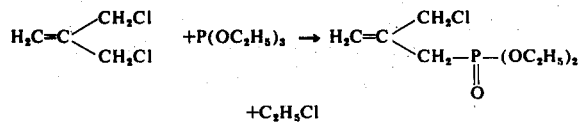

or

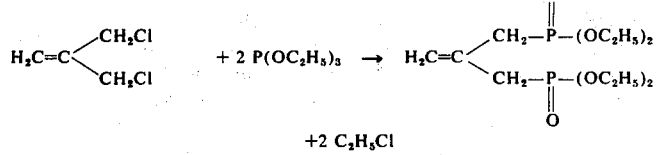

The 1,3-dihalogen-2-methylene propane used as starting material can readily be prepared from 2-methylene-1,3-propane diol and, for example, thionyl chloride (where the halogen is chlorine). This compound can also be obtained from the corresponding diol and hydrogen chloride in an organic solvent, for example in accordance with the following reaction:

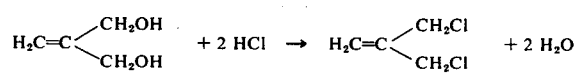

Preparation of the diol is known in the art. 2-methylene-1,3-propane diol can readily be obtained, for example, by reacting together isobutylene, oxygen and acetic acid, followed by hydrolysis of the acetyl groups.

In the case of the monophosphonic acid, the dihalogen compound is initially introduced and thereafter the triester of phosphorous acid is added dropwise at temperatures of from 110° to 160°C. The reaction is preferably carried out in the absence of solvents. The molar ratio of the dihalogen compound to the phosphite amounts to between 1:1 and 3:1. The reaction is carried out at temperatures in the range of from 110° to 200°C, the alkyl halide formed during the reaction where a trialkyl phosphite is used as reactant being contintuously distilled off. In order to complete the reaction, the reaction temperature can be maintained for another 3 to 4 hours following the dropwise addition.

To prepare the bis-phosphonic acid, the starting compounds in a molar ratio of diahlide to phosphite of from 1:2 to 1:4 are heated together to temperatures of from 120° to 220°C. In this case, too, the corresponding alkyl halide is removed from the reaction mixture by distillation, optionally with the assistance of an inert gas such as $N_2$, where trialkyl esters of phosphorous acid are used as reactant.

The reaction is completed when no more halide is evolved. If the dihalide is reacted with triaryl phosphites, the reaction product is worked up by conventional methods. On completion of the reaction, the more readily volatile constituents are distilled off in a water-jet vacuum both in the case of the monophosphonic acid ester and in the case of the bis-phosphonic acid ester. The reaction products can be recovered by conventional methods, for example by distillation in a high vacuum. The yields amount to between 65 and 80%, based on the phosphite used.

A further object of the invention are acrylonitrile copolymers which comprises 60 to 99.9% by weight of acrylonitrile, the balance being up to 39.9% by weight of ethylenically unsaturated with acrylonitrile copolymerizable/comonomers and/or 0.1 to 40% by weight of a copolymerized 2-methylene propane phosphonic acid ester of the formula:

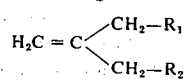

in which $R_1$ represents halogen Cl, Br, I or the radical

and $R_2$ the radical

where $R_3$ is hydrogen, $NH_4$ an alkali metal, a linear or branched, substituted or unsubstituted $C_1$-$C_4$-alkyl, aryl, halogen- or alkyl-substituted aryl and $R_4$ hydrogen a linear or branched, substituted or unsubstituted $C_1$-$C_4$-alkyl, aryl optionally substituted by halogen or alkyl, said acrylonitrile copolymers having K-value according to Fikentscher in the range of from 60 to 120. Acrylonitrile copolymers are prefered comprising 60 to 90% by weight of acrylonitrile, 5 to 35% by weight of an ethylenically unsaturated, with acrylonitrile copolymerizable comonomer and 5 to 35% by weight of a copolymerized 2-methylene propane phosphonic acid ester preferably the K-values are in the range of 70 to 105.

The copolymerisation of ethylenically unsaturated compounds such as acrylonitrile, (meth) acrylic acid esters, 2-methylene propane-1,3-dichloride, vinyl chloride, vinylidene chloride or mixtures of these comonomers and 2-methylene propane-phosphonic acid derivatives can be carried out by polymerising the monomers in solution and also in dispersion or suspension. 1-chloro-2-methylene propane-3-phosphonic acid diethyl ester and/or 2-methylene propane-1,3-bis-phosphonic acid tetraethyl ester are preferably used as starting compounds for copolymerization.

It was surprising that substances of the above general formula should lend themselves to polymerization with unsaturated compounds to form polymers with such good K-values (Fikentscher, Cellulosechemie 13, 58, 1932) in such high yields particularly since homopolymerisation was not possible and because substances of this type had been expected to show a negative effect as regulators in copolymerization reactions. It was also surprising that the copolymerization reaction should lead to products that are highly soluble, for example, in dimethylformamide, in other words that polymerization should not be accompanied by crosslinking although the phosphorus compounds used, corresponding to the above general formula, show a substituted methallyl structure which is known to have a general tendency towards crosslinking in polymerization reaction. Solution polymerization is carried out in the usual solvents such as dimethylformamide and nitric acid. Where polymerization is carried out in dimethylformamide, radical formers, such as azo-bis-isobutyronitrile, can be present as known per se. Where polymerization is carried out in nitric acid, it is possible in the usual way to use, for example, acetyl acetonates and oxidising agents, such as ammonium peroxy disulphate, as polymerization initiators. The total quantity of the initiator and, where a redox system is used, the quantitative ratio of the oxidizing agent to the reducing agent and the concentration of the monomers in the polymerization solution are selected in accordance with the data frequently published in the literature.

Precipitation polymerizations can be carried out in diluents such as, for example, water, low aliphatic alcohols and benzenes. Preferably polymerization is carried out in an aqueous suspension or emulsion. It is advantageous in some cases to add emulsifiers or suspending agents. Where polymerization is carried out in water, as is preferably the case, conventional redox systems such as, for example, persulphate/bisulphite, are used as initiators. The quantitative ratio of the oxidizing agent to the reducing agent is from 12:1 to 1:15 and preferably from 8:1 to 1:12. The total quantity of initiator amounts to between 0.1 and 15% by weight, based on the total monomer content and preferably to between 1 and 10% by weight.

Polymerization is carried out in the acid range, preferably at pH-values of from 1.5 to 5, and at temperatures of from 0° to 90°C and preferably from 20° to 55°C, over reaction times which can vary from 1 hour to several days. The ratio by weight of total monomer to diluent amounts to between 1:2 and 1:25, preferably to between 1:5 and 1:15.

The copolymers according to the invention contain different quantities of each comonomer, copolymerization being carried out with starting mixtures containing from 0.1 to 40% by weight of the compounds of the above general formula, namely the mono or bis-phosphonates either on their own or mixed with one another in any ratio. Accordingly, the proportion of ethylenically unsaturated compounds, such as acrylonitrile, (meth) acrylic acid esters, 2-methylene propane-1,3-dichloride, vinyl chloride, vinylidene chloride or mixtures of these comonomers, amounts to between 60 and 99.9% by weight at the beginning of polymerization, this figure once again applying either to an individual substance or to a mixture of unsaturated compounds. In the case of precipitation polymerizations, the copolymers are isolated by filtration, which is preceded in the case of some polymerization reactions by precipitation of the polymer, for example by adding a saturated solution of a strong electrolyte, such as sodium chloride, sodium sulphate, zinc sulphate or calcium chloride. Alternatively, precipitation is carried out by adding a small quantity of an electrolyte to the monomer dispersion before the reaction is initiated.

In the case of solution polymerizations, the polymer is separated off in the conventional way, for example by stirring the polymer solution into a precipitant, such as water or of lower aliphatic alcohols, followed by filtration. The yields amount to between 60 and 98% by weight, based on the total monomer content, while the K-value amounts to between 60 and 120.

A further object of the invention are fibers and films of the acrylonitrile/2-methylene propane phosphonic acid copolymers and of mixtures thereof with other polymers. Fibers and films can be prepared by spinning or casting a solution of the copolymer in an organic solvent p.i. dimethyl formamide.

The articles produced from the copolymers according to the invention are flame-resistant, i.e. substantially non-inflammable, they show increased thermal stability, improved affinity for dyes and fastness to light and, in some cases, they exhibit better pilling behaviour.

The LOI-values (limited oxygen index) quoted in the following Examples were determined by the so-called oxygen burning test. The apparatus used to carry out the oxygen burning test consists of a burning tube having a laterally attached nozzle through which an oxygen/nitrogen gas mixture flows and about one third of which is filled with glass beads in order to improve admixture of the gases. Fine-regulating valves accurately regulate the oxygen and nitrogen which flow through gas-flow meters. The oxygen and nitrogen are taken from the gas cylinders with pressure-reducing valves which are provided for this purpose. A needle frame is used as the specimen holder.

After the specimen holder has been set up with the specimen depending into the burning tube, the specimen is exposed from above to a gas flame. The mixing ratio of oxygen to nitrogen is varied until the specimens burns uniformly downwards with a minimum flame. The burning value $n$ is calculated as follows:

$$n = \frac{\text{liters of } O_2/h}{\text{liters of } O_2/h + \text{liters of } N_2/h}$$

Test specimens:
Webs produced from fibers obtained by conventional spinning methods.
Dimensions of the test specimens:
Length 11 cm
Width 9.5 cm Before testing, all the materials to be tested are laid out for 24 hours in air at 20°C/65% relative humidity.

The following Examples illustrate more particularly the invention.

EXAMPLE 1

351 parts by weight of acrylonitrile, 29 parts by weight of methyl acrylate and 20 parts by weight of 1-chloro-2-methylene propane-3-phosphonic acid diethyl ester are taken up in 5000 parts by volume of water. The pH-value is adjusted to 3.0 with dilute acid and polymerization is initiated at 50°C. by the addition with stirring of 3 parts by weight of potassium persulphate and 5 parts by weight of sodium metabisulphite to the reaction mixture while nitrogen is passed through. After 7 hours, the polymer is filtered off under suction, washed with water and methanol and dried in vacuo at 50°C until constant in weight. Yield: 380 parts by weight (95%), K-value: 78.

The polymer is spun into fibers which are subsequently processed to form a web with the dimensions specified above. LOI-value $n = 0.212$.

Comparison Example 1

A copolymer of 93.8% by weight of acrylonitrile, 5.5% by weight of methyl acrylate and 0.7% by weight of sodium methallyl sulphonate with a K-value of 83.8 is spun into fibers which are subsequently processed into a web. LOI-value: $n = 0.200$.

EXAMPLE 2

332 parts by weight of acrylonitrile, 28 parts by weight of methyl acrylate and 40 parts by weight of 1-chloro-2-methylene propane-3-phosphonic acid diethyl ester are added while stirring to 5000 parts by volume of water. The pH-value is adjusted to 3.0 with dilute sulphuric acid after the reaction mixture has been heated to 50°C. Polymerization is initiated by the addition of 3 parts by weight of potassium persulphate and 5 parts by weight of sodium metabisulphite to the reaction mixture while nitrogen is continuously passed through. After 3.5 hours, a further 1.5 parts by weight of potassium persulphate and 3.5 parts by weight of sodium metabisulphite are added. The total polymerization time amounts to 7 hours. The polymer is then filtered off under suction, washed with water and methanol and dried in vacuo at 50°C until constant in weight.

Yield: 355 parts by weight (88.7%), K-value: 86.5. LOI-value (web): $n = 0.250$. LOI-value (comparison example 1): $n = 0.200$.

EXAMPLE 3

The polymerization of 265 parts by weight of acrylonitrile, 20 parts by weight of methyl acrylate and 15 parts by weight of 2-methylene propane-1,3-bis-phosphonic acid tetra-ethyl ester in 4000 parts by volume of water is initiated at 50°C/pH-3.0 (dilute sulphuric acid) by the addition of 4 parts by weight of potassium persulphate and 4 parts by weight of sodium metabisulphite while nitrogen is continuously passed through. After 7 hours, the polymer is filtered off under suction, washed with water and methanol and dried in vacuo at 50°C.

Yield: 250 parts by weight (83.4%).
K-value: 85.7.
LOI-value (web): $n = 0.212$.
LOI-value (comparison example 1): $n = 0.200$.

EXAMPLE 4

260 parts by weight of acrylonitrile, 20 parts by weight of methyl acrylate and 31.1 parts by weight of 2-methylene propane-1,3-bis-phosphonic acid tetra-ethyl ester are polymerized in 4000 parts by volume of water as in Example 3. Yield: 288 parts by weight (74.4%), K-value: 84.3

EXAMPLE 5

260 parts by weight of acrylonitrile, 20 parts by weight of methyl acrylate and 70 parts by weight of 2-methylene propane-1,3-bis-phosphonic acid tetra-ethyl ester are polymerized in 4000 parts by volume of water as in Example 3.

Yield: 215 parts by weight (61.5%), K-value: 86.4 LOI-value (web): $n = 0.287$ LOI-value (comparison example 1): $n = 0.200$

EXAMPLE 6

88 parts by weight of acrylonitrile, 7 parts by weight of methyl acrylate, 2.5 parts by weight of 1-chloro-3-methylene propane-3-phosphonic acid diethyl ester and 2.5 parts by weight of 2-methylene propane-1,3-bis-phosphonic acid tetra-ethyl ester are heated to 50°C with stirring in 1200 parts by volume of water while nitrogen is passed through. After the pH-value has been adjusted to 3.0 with dilute sulphuric acid, polymerization is initiated by the addition of 1 part by weight of potassium persulphate and 1 part by weight of sodium metabisulphate. After 6 hours, the polymer is filtered off under suction, washed thoroughly with water and methanol and dried in vacuo at 50°C.

Yield: 92.5 parts by weight (92.5%). K-value: 90.

EXAMPLE 7

82 parts by weight of acrylonitrile, 7 parts by weight of methyl acrylate, 5 parts by weight of 1-chloro-2-methylene propane-3-phosphonic acid diethyl ester and 5 parts by weight of 2-methylene propane-1,3-bis-phosphonic acid tetra-ethyl ester are polymerized in 1200 parts by volume of water as described in Example 6.

Yield: 76 parts by weight (76%). K-value: 101.8.

EXAMPLE 8

73 parts by weight of acrylonitrile, 7 parts by weight of methyl acrylate, 10 parts by weight of 1-chloro-2-methylene propane-3-phosphonic acid diethyl ester and 10 parts by weight of 2-methylene propane-1,3-bis-phosphonic acid tetraethyl ester are polymerized in 1200 parts by volume of water as described in Example 6, except that a further 0.5 part by weight of potassium persulphate and 0.5 part by weight of sodium metabisulphite are added after polymerization has been in progress for 3 hours.

Yield: 63.5 parts by weight (63.5%). K-value: 87.8.

EXAMPLE 9

A mixture of 60 parts by weight of acrylonitrile, 35 parts by weight of vinylidene chloride, 5 parts by weight of 1-chloro-2-methylene propane-3-phosphonic acid diethyl ester and 12 parts by volume of a 25% aqueous solution of phenyl-(3-methacrylamino)-phenyl disulphimide in 1200 parts by volume of water is adjusted to a pH value of 3 by addition of dilute sulphuric acid at 28°C. After the air has been displaced by nitrogen, polymerization is initiated by the addition of 2 parts by weight of potassium persulphate and 4 parts by weight of sodium metabisulphate. After 5 hours, the polymer is filtered off under suction and the polymer is processed as described above.

Yield: 73 parts by weight (73%). K-value: 87.1.

EXAMPLE 10

The monomer mixture described in Example 9 is polymerized in 800 parts by volume of water under the same reaction conditions as in Example 9.

Yield: 95 parts by weight (95%). K-value: 80.7.

EXAMPLE 11

In a three-necked flask equipped with a stirring mechanism and reflux condenser and which has been flushed free from air with nitrogen, 60 parts by weight of acrylonitrile, 27 parts by weight of vinylidene chloride, 10 parts by weight of 1-chloro-2-methylene propane-3-phosphonic acid diethyl ester and 12 parts by volume of a 25% aqueous solution of phenyl-(3-methacrylamido)-phenyl disulphimide are mixed with 500 parts by volume of water and, after heating to 28°C, adjusted to pH 3.0. Polymerization is then initiated by the addition of 5.8 parts by weight of potassium persulphate and 1.7 parts by weight of sodium metabisulphite. The polymer is filtered off under suction after 5 hours and processed as described above.

Yield: 78 parts by weight (78%). K-value: 76.5.

EXAMPLE 12

504 parts by weight of acrylonitrile, 256 parts by weight of vinylidene chloride and 40 parts by weight of 2-methylene propane-1,3-bis-phosphonic acid tetra-ethyl ester are taken up in 8000 parts by volume of water, heated to 28°C and polymerization is initiated under a nitrogen atmosphere at pH 3.0 by the addition of 7.2 parts by weight of sodium metabisulphite and 0.6 parts by weight of potassium persulphate. The resulting polymer is filtered off under suction after 5 hours and worked up as described above.

Yield: 624 parts by weight (78%). K-value: 82.8. LOI-value (web): $n = 0.287$. LOI-value (comparison example 1): $n = 0.200$.

EXAMPLE 13

504 parts by weight of acrylonitrile, 176 parts by weight of vinylidene chloride and 120 parts by weight of 2-methylene propane-1,3-bis-phosphonic acid tetraethyl ester are polymerized in 8000 parts by volume of water under the conditions described in Example 12. A further 3.6 parts by weight of sodium metabisulphite and 0.3 part by weight of potassium persulphate are added after the polymerization has been in progress for 2.5 hours. The total polymerisation time amounts to 5 hours.

Yield: 510 parts by weight (64%). K-value: 81.1. LOI-value (web): $n = 0.315$. LOI-value (comparison example 1): $n = 0.200$.

The web of this Example was also compared with a web consisting of 60% by weight of acrylonitrile, 37% by weight of vinylidene chloride, 3% by weight of phenyl-(3-methacrylamino)-phenyl disulphimide (K-value = 80.6).

LOI-value: $n$-0.275

EXAMPLE 14

85 parts by weight of acrylonitrile, 5 parts by weight of 2-methylene propane-1,3-dichloride and 10 parts by weight of 1-chloro-2-methylene propane-3-phosphonic acid diethyl ester are polymerized under nitrogen in 1000 parts by volume of water at a temperature of 50°C and at a pH-value of 3.0 by the addition of 1 part by weight of potassium persulphate and 1 part by weight of sodium metabisulphite. The total polymerization time amounts to 7 hours. After the polymer has been filtered off under suction, it is washed thoroughly with water and methanol and dried in vacuo at 50°C.

Yield: 76 parts by weight (76%). K-value: 78.6.

EXAMPLE 15

The polymerization of 80 parts by weight of acrylonitrile, 10 parts by weight of 2-methylene propane-1,3-dichloride and 10 parts by weight of 2-methylene propane-1,3-bis-phosphonic acid tetra-ethyl ester in 1000 parts by volume of water is initiated under a nitrogen atmosphere at a temperature of 50°C and at a pH-value of 3.0 by the addition of 1 part by weight of potassium persulphate and 1 part by weight of sodium metabisulphite. After 7 hours, the resulting polymer is filtered off under suction, washed and dried as described above.

Yield: 70.1 parts by weight (70.1%). K-value: 86.3.

Preparation of the phosphonic acid esters

EXAMPLE A 1-chloro-2-methylene propane-3-phosphonic acid diethyl ester 34 parts by weight of 2-methylene propane-1,3-dichloride are heated to 135°C, after which 30 parts by weight of triethyl phosphite are added dropwise with stirring, Ethyl chloride distills off continuously during the dropwise addition. On completion of the dropwise addition, the reaction temperature is increased slowly to 180°C. After 3 to 4 hours at 180°C, the evolution of ethyl chloride is at an end and the reaction is over. The excess dihalide is distilled off in a water-jet vacuum. The resulting 1-chloro-2-methylene propane-3-phosphonic acid diethyl ester is distilled off in a high vacuum.

Yield: 30.7 parts by weight (75% of the theoretical, based on triethyl phosphite) b.p: 83°–90°C/0.05 Torr N20/D: 1.4599 Analysis: $C_8H_{16}ClO_3P$ (226.6).

|  | C | H | Cl | O | P |
|---|---|---|---|---|---|
| Calculated: | 42.3% | 7.1% | 15.7% | 21.2% | 13.7% |
| found: | 42.4% | 6.3% | 15.7% | 21.5% | 14.1% |
|  | 42.4% | 6.3% | 15.7% | 21.7% | 13.9% |

EXAMPLE B 2-methylene propane-1,3-bis-phosphonic acid tetra-ethyl ester 50 parts by weight of 2-methylene-1,3-propane dichloride and 140 parts by weight of triethyl phosphite are heated with stirring to 150°C. The reaction temperature is slowly increased to 180°C and the reaction mixture is maintained at this temperature until no more ethyl chloride can be collected in a following cold trap. Thereafter the more readily volatile constituents are distilled off in a water-jet vacuum. The reaction product is recovered by distillation in a high vacuum.

Yield: 105 parts by weight (80% of the theoretical, based on triethyl phosphite) b.p.: 157– 159°C/0.02 Torr N20/D: 1.4542

Analysis: $C_{12}H_{26}O_6P_2$ (328.3)

|  | C | H | O | P |
|---|---|---|---|---|
| Calculated: | 43.9% | 7.9% | 29.3% | 18.9% |
| Found: | 43.5% | 8.1% | 29.3% | 19.1% |
|  | 43.3% | 8.0% | 29.6% | 18.9% |

What we claim is:

1. An acrylonitrile copolymer comprising: 1. 60–99.9% by weight of acrylonitrile; 2. 0.1–40% by weight of 2-methylene propane phosphoric acid ester of the formula

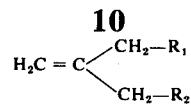

wherein $R_1$ = chloro, bromo, iodo, or

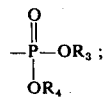 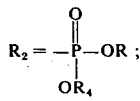

$R_3$ = hydrogen, ammonium, alkali metal, $C_1$-$C_4$-alkyl, or aryl;

$H_4$ hydrogen, $C_1$-$C_4$-alkyl, or aryl; and 3. the remainder being an ethylenically unsaturated comonomer copolymerizable with acrylonitrile; said copolymer having a K-value of 60–120 as described by Fikentscher in Cellulosechemic 13, 58 (1932).

2. The acrylonitrile copolymer of claim 1, wherein said 2-methylene propane phosphonic acid ester is 1-chloro-2-methylene, propane-3-phosphonic acid diethyl ester.

3. The acrylonitrile copolymer of claim 1, wherein said 2-methylene propane phosphonic acid ester is 2-methylene propane-1,3-bis-phosphonic acid tetra-ethyl ester.

4. The acrylonitrile copolymer of claim 1, wherein said ethylenically unsaturated comonomer is methylacrylate.

5. The acrylonitrile copolymer of claim 1, wherein said ethylenically unsaturated comonomer is vinylidene chloride.

6. The acrylonitrile copolymer of claim 1, wherein said ethylenically unsaturated comonomer is 2-methylene propane-1,3-dichloride.

7. Fibers or films of the copolymer of claim 1.

8. A process for the production of an acrylonitrile copolymer having at least 60 % by weight of copolymerized acrylonitrile copolymer which comprises polymerizing acrylonitrile together with a 2-methylene propane phosphonic acid ester in an aqueous medium at a $p_H$ value of from 2 to 7 and at a temperature of from 0° to 90°C in the presence of a redox initiator system comprising a peroxy compound and a sulphur compound of low stage of oxidation.

9. The process of claim 8 wherein the polymerizing is effected in the presence of an ethylenically unsaturated comonomer copolymerizable with acrylonitrile.

* * * * *